United States Patent
Kulmala et al.

(10) Patent No.: US 8,920,718 B2
(45) Date of Patent: Dec. 30, 2014

(54) METHODS AND DEVICES TO GENERATE LUMINESCENCE FROM INTEGRATED ELECTRODE CHIPS BY CATHODIC AND BIPOLAR PULSES

(75) Inventors: Sakari Kulmala, Kirkkonummi (FI);
Timo Kalevi Korpela, Turku (FI);
Jarkko Uolevi Eskola, Turku (FI);
Teppo Tapani Laaksonen, Turku (FI)

(73) Assignee: Labmaster Oy, Turku (FI)

( * ) Notice: Subject to any disclaimer, the term of this patent is extended or adjusted under 35 U.S.C. 154(b) by 83 days.

(21) Appl. No.: 13/703,453

(22) PCT Filed: Jun. 10, 2011

(86) PCT No.: PCT/FI2011/000030
§ 371 (c)(1),
(2), (4) Date: Jan. 17, 2013

(87) PCT Pub. No.: WO2011/154588
PCT Pub. Date: Dec. 15, 2011

(65) Prior Publication Data
US 2013/0199945 A1 Aug. 8, 2013

(30) Foreign Application Priority Data

Jun. 11, 2010 (FI) .................................. 20100246

(51) Int. Cl.
*G01N 27/327* (2006.01)
*G01N 21/66* (2006.01)

(52) U.S. Cl.
CPC ............ *G01N 27/3276* (2013.01); *G01N 21/66* (2013.01)
USPC ............ 422/52; 422/82.08; 435/7.1; 435/6.1; 436/501; 436/172; 204/400; 205/775

(58) Field of Classification Search
CPC .................... G01N 21/66; G01N 27/3276
USPC ............ 205/775, 780.5, 792; 204/400; 422/82.01, 68.1, 52, 82.08; 435/287.1, 435/6.1, 7.1; 436/501, 172
See application file for complete search history.

(56) References Cited

U.S. PATENT DOCUMENTS

| 6,140,045 | A | * | 10/2000 | Wohlstadter et al. | ........ 435/6.11 |
| 6,251,685 | B1 | * | 6/2001 | Dorsel et al. | .................. 436/172 |
| 6,251,690 | B1 | | 6/2001 | Kulmala | |
| 6,521,181 | B1 | * | 2/2003 | Northrup et al. | ................. 506/33 |
| 7,005,108 | B2 | | 2/2006 | Ala-Kleme et al. | |
| 7,341,834 | B2 | * | 3/2008 | Yang | ............................ 435/6.12 |
| 2009/0178924 | A1 | * | 7/2009 | Ala-Kleme et al. | ..... 204/403.06 |

FOREIGN PATENT DOCUMENTS

JP 2009204375 A 10/2009

OTHER PUBLICATIONS

Niskanen et al.—Sensors and Actuators B 152 (2011) 56-62.*
Spehar-Deleze et al.—Electrochimica Acta 51 (2006) 5438-5444.*
Eskola et al.—Journal of Luminescence 118 (2006) 238-244.*
Kulmala—Powerpoint presentation Nov. 2, 2010.*

(Continued)

*Primary Examiner* — Jennifer Dieterle
(74) *Attorney, Agent, or Firm* — Gearhart Law, LLC (57) ABSTRACT

The invention describes novel chemiluminescence electrode devices and their novel properties to enable achieving luminescence signal by electrical excitation by cathodic or bipolar pulses in aqueous electrolyte solutions. These devices form a significant improvement in construction of cheap and reliable means for especially diagnosis of health conditions in point-of-need purposes.

9 Claims, 4 Drawing Sheets

(56) References Cited

OTHER PUBLICATIONS

Suomi (Journal of Electroanalytical Chemistry 586 (2006).*
Wu et al.—Electroanalysis 2010, 22, No. 22, 2702-2707.*
PCT/FI2011/000030—International Search Report; Oct. 3, 2011 (7 pgs).
Niskanen, A.J. et al; Ultrathin tunnel insulator films on silicon for electochemiluminescence studies; http://www.sciencedirect.com/science?_ob=ArticleListURL&_method=list&_ArticleListID=415461684&_sort=r&_st=13&view=c&_acct=C000228598&_version=1&_urlVersion=0&_userid=10&md5=14c217a3f08c8e4346a671658c2&searchtype=a (abstract), 2009.
Niskanen, A.J. et al; Integrated microelectrode hot electron electrochemiluminescent sensor for mircofluidic applications; http://www.sciencedirect.com/science/article/pii/S0925400510007689 (abstract), 2011.

* cited by examiner

SEQUENCE LISTING

```
<160> NUMBER OF SEQ ID NOS: 2

<210> SEQ ID NO 1
<211> LENGTH: 26
<212> TYPE: DNA
<213> ORGANISM: artificial sequence
<220> FEATURE:
<223> OTHER INFORMATION: chemically synthesized

<400> SEQUENCE: 1
ttagccgcat tcaggggcg aaaaaa                                          26

<210> SEQ ID NO 2
<211> LENGTH: 21
<212> TYPE: DNA
<213> ORGANISM: artificial sequence
<220> FEATURE:
<223> OTHER INFORMATION: chemically synthesized

<400> SEQUENCE: 2
gaaacacgga cacccaaagt a                                              21
```

METHODS AND DEVICES TO GENERATE LUMINESCENCE FROM INTEGRATED ELECTRODE CHIPS BY CATHODIC AND BIPOLAR PULSES

PRIORITY

This application is a national entry of PCT/FI2011/0000030 filed on Jun. 10, 2011 which claims priority of FI20100246 filed on Jun. 11, 2010, both of which are fully incorporated herein by reference.

SEQUENCE LISTING

This application contains sequence data provided on a computer readable diskette and as a paper version. The paper version of the sequence data is identical to the data provided on the diskette.

FIELD OF INVENTION

The invention belongs to methods by which amount of molecules generating luminescence light is measured quantitatively at an extremely low concentrations in aqueous solutions. The field of utilization of the invention is measurement of biological molecules from samples taken from humans or animals aiming at analyzing their health conditions. The invention describes new improved methods to manufacture and use of test devices for such analyses.

BACKGROUND OF INVENTION

Presently, there is a general burden need for fast, sensitive and quantitative diagnostic technologies. Such ones are suitable for wide market areas including public health, research, farming, environmental care, veterinary medicine, and certain industrial production areas. Improved sensitivity, speed, robustness, stability, and decreased cost per analysis are factors, which after being accomplished in diagnostic technologies can find applications in quite new areas.

Very high sensitivity can be obtained with certain diagnostics instruments, but they are too expensive. On the other hand, certain methods can be enough inexpensive, exemplified by immunochromatography, but they are not applicable to fully quantitative applications of the market. Any technology, wherein a set of satisfactory demands are met, will have an important place in the future diagnostics and a huge market potential.

There are a number of different analytical principles in practical use in diagnostics: for example, assays based on radioactivity, enzyme-linked immunosorbent assay (ELISA), colorimetric assays, and assays based on fluorescence, and chemiluminescence including anodic as well as hot electron-induced (cathodic) electrochemiluminescence (ECL). The hot electron-induced ECL is described in detail in U.S. Pat. No. 6,251,690, Kulmala S., et al. Each of these techniques has their role as regards to the integral of sensitivity, robustness, stability, speed, and price. The differences between the techniques reflect the function of physical limitations or advantages of the methods. For example, a drawback of the application based on radioactive compound is the decay of the label within a period of time and the extra cost of radioactive waste from both the safety and environmental viewpoint. The application of the most sensitive assays on diagnostics is limited by the complicated nature of the tests and instruments, and only experts can perform the assays. The complexity of the assay is generally directly proportional to the price of the instrument and/or the test. In the context of complex instruments, it could be mentioned the anodic electrochemiluminescence techniques now becoming more and more popular: the instrument is a complicated laboratory robot, the handling of which needs expertise and where the measuring process involves repeated washes and preparative steps. They are factors that increase the cost of the analyses as well as increase the amount of waste and therefore will make this method impossible for the needs of small laboratories, doctors offices etc. (bedside or point of care analytics).

Commercially beneficial methods are based on the principle that the substances to be analyzed are identified and measured in mixtures by so-called label substances. In the measurements based on unique properties of biological molecules, as in immunochemical assays, the analyte to be measured (X) can be selectively sorbed from a mixture of molecules to solid-phase bound antibodies and then the bound molecules are measured with another labeled antibody selectively binding to (X). The label substances can be radioactive isotopes, enzymes, light absorbing, fluorescent or phosphorescent molecules, certain metal chelates etc., which are linked covalently to the antibody. Alternatively, the purified (X) can be marked and the amount of unknown unlabeled sample (X) can be measured by a competition reaction. The assays for DNA and RNA can be also based on the selective binding (bioaffinity). Also many other chemical and biochemical analyses can be carried out by the same principles. In order to decrease the cost and/or increase the measuring accuracy, there is presently a tendency to measure several different parameters at the same time in the sample. One possibility is to use labels fluoresceing or phosphoresceing (luminating) at different wavelength or possessing different fluorescence lifetimes. Different measuring principles and strategies, which can be used in immunodiagnostics, have been described in the book The Immunoassay Handbook, Edited by David Wild, Stockton Press Ltd., New York, 1994, on pages 1-618.

It is known in the prior art that organic substances and metal chelates are beneficial as label substances and that they can be excited by light or by electrochemically to produce luminescence specific to the label. These methods are particularly sensitive and feasible. However, because the measured concentrations are extremely low, there are also case-dependent difficulties; the use of fluorescence can be disturbed, among other things, by Tyndall, Rayleigh and Raman scattering. When measuring biological substances, there is, almost without exception, after the excitation pulse, a fast-discharging high background fluorescence. Phosphorescence in the solution phase can be utilized mostly only with chelates between lanthanide ions and specially synthesized organic molecules. The drawback of the excitation techniques with the photoluminescent labels is the complexity of the instruments and the high price of the sensitive optical components.

In general, the advantage of ECL is the low price of the electrical excitation components and simpler optics. Thus, compared to the photoluminescence, several drawbacks can be avoided. Traditional anodic electrochemiluminescence with inert metal electrodes can be carried out with organic luminophores by a relative simple instrument in non-aqueous solvents. However, in bioaffinity assays, where the biggest commercial expectations are concentrated to, water solutions are applied. Biological samples are taken nearly always in non-organic solutions and therefore the measuring system should work in aqueous or at least in micellar water solutions.

Only a very limited number of transition metal chelates are working as ECL-labels in anodic ECL in water or micellar solutions.

Thus far the commercially most important analytical chemical application of the anodic ECL is the method using derivatives of Ru(bpy)$_3^{2+}$-chelate, where the detection phase of the label occurs in micellar phase. As known from textbooks, the micellar mixtures are always prone to different disturbing effects due to the uncontrolled complexity of the micellar equilibria. Thus, the hot electron-induced ECL, which does not depend on micelles has many crucial advantages over the anodic ECL. It can be applied both to immuno- and DNA hybridization methods (see, Blackburn, G., et al., 1991, Clin. Chem. 37: 1534-1539; Kenten, J., et al. 1992, Clin. Chem. 33: 873-879). The immunoassays and DNA or RNA probe applications by Roche Diagnostics Ltd. exploit magnetic particles by which the label substance is brought onto golden working electrode (Massey; Richard J., et al. U.S. Pat. No. 5,746,974; Leland; Jonathan K., et al. U.S. Pat. No. 5,705,402). The reproducible handling of magnetic latex particles is however in many ways difficult, therefore this method is useful only in expensive laboratory robots (e.g. Elecsys 1010 and 2010) having a complicated and precise liquid handling system. In addition, the permanent massive golden work electrode needs long cleaning and pretreatment between each analysis (Elecsys Service Manual, p. 70).

It was found out that a significant improvement in the performance could be acquired with placing a thin porous film on the work electrode, and by producing CIPF-devices (see patent US2009178924, Ala-Kleme et al.). However, these kind CIPF devices had a serious drawback in that they need a separate counter electrode in the measurement instrument and careful washing steps between each analysis because the same electrolytic cell containing the counter electrode has to be repeatedly used.

In HECL work electrode, the hot electrons are considered to tunnel from the closest parts of the electrode from the counter electrode, which means electrode edges in case of planar electrodes in the same plain because theoretically the tunneling of electrons shall happen from places which has highest tunneling probability (see Kulmala S., Suomi J, Analytica Chimica Acta 500 (2003) 21-69). If the tunneling will take place from such edges and even if a detectable luminescence will occur, such a local luminescence would not be useful as the work electrode aimed at the diagnostics purposes of the present invention because such luminescence would not be dependent on the concentration of the label compounds bound to the surface of the electrode, or at least, the relationship would be only marginal. Thus, a person skilled in the art would not try to construct electrodes wherein the work and counter electrodes are fabricated on approximately same level on a flat surface if HECL is applied. If the electrons are tunneled from sharp edges, it follows that it is extremely difficult to control the manufacturing process so that the different electrodes would function reproducible, the fact what is absolutely necessary for diagnostic test chips.

In the present invention, we surprisingly found that it is possible to construct even completely planar integral work and counter electrodes which have a very high performance in bioaffinity assays. This appeared to be result from materials used in the electrodes and the proper dimensions of the thickness of the electrolyte solution above the electrodes as well geometrical arrangements of the electrodes themselves. This finding led also to a completely new property of the electrodes which enable further increase of the electrode performance over the present situation. We surprisingly found that the described construction with certain electrode materials allowed the use of bipolar pulses for luminescence excitation, meaning that cathode and anode can be repeatedly changed as to their position either repeatedly or after a certain pulse trains. This allows exploiting the surface of both electrodes for the analysis purposes. For example, the light pulses from one electrode can be compared to the other one and such a system serves as an internal standard, or two analytes can me measured simultaneously.

According to then present invention a significant quantitative and qualitative improvement of the ECL electrodes was achieved as illustrated in the patent claims 1-10.

BRIEF DESCRIPTION OF DRAWINGS

FIG. 3. Calibration curves of a terbium (III) chelate. Tb(III) chelated with 2,6-bis[N,N-bis(carboxymethyl)aminomethyl]-4-bentsoylphenol was used as a model of Tb(III) chelates (see Example 1). (a) Curve obtained by using EChips of type described in FIG. 1 wherein both the work electrode and counter electrode areas are first manufactured by vacuum evaporation of aluminum through a mask. Then the electrodes are oxidized in air and silver ink is added on top of the counter electrode areas using mask and painting or screen-printing. The results are marked with closed circles. (b) Curve obtained by using EChips described in (a) except an additional carbon paste layer is painted or screen printed on top of the silver ink layer, the results marked with open circles. (c) Curve obtained by using EChips of type described in FIG. 2 wherein a large silicon chip is first coated with 4-nm thermal oxide film, then an adhesive tape with three holes for work electrode area is glued onto the electrode and the a counter electrode pattern is first painted using mask with silver ink and secondly an additional layer of carbon paste, the results are marked with closed triangles. (d) Curve obtained by using EChips of type described in FIG. 1 wherein both the work electrode and counter electrode areas are first manufactured by vacuum evaporation of aluminum through a mask Then the electrodes are oxidized in an oxygen atmosphere at room temperature and an ultra thin polymer is added on top of the electrode areas using ink jetting, or as in this case, dipping in the dissolved organic polymer such as polystyrene dissolved in toluene; results marked with squares.

FIG. 5. Viral RNA assay. The measurements were done using a membrane of a standard Labmaster CIPF device containing all the required hybridization reagents in dry state on top of the work electrode and counter electrode areas of the type of EChip described in FIG. 2 (see Example 3).

DETAILED DESCRIPTION OF THE INVENTION

Definitions

Work electrode means here the electrode producing luminescence when electrons are tunneling through an insulator film over the conducting material (thus normally cathode)

Counter electrode is the other electrode in the HECL cell. In HECL it is normally made of conductive material, usually of a metal. In the present invention a material of higher resistivity, like a carbon paste, can also cover the metal base. This invention brings about new properties to the HECL system.

EChip means here an ECL electrode in which anode and cathode are both located on the same base/support material integrally connecting anode and cathode.

Planar EChip means that anode and cathode are manufactured practically on the same level close to each others.

Cathodic pulse means an electrical pulse which gives negative polarity to the work electrode of an electrolytic cell.

Anodic pulse means an electrical pulse which gives positive polarity to the work electrode of an electrolytic cell.

Bipolar pulse train or bipolaric pulsing is only possible in HECL using selected electrodes of the present invention. Bipolar pulsing means that the polarity of work electrode and counter electrode are changed either after each pulse or after a set of pulses.

CIPF means a work electrode covered by a thin porous film used to make bioaffinity reaction over the electrode fast.

According to the present invention, different analyses can be performed with simple and inexpensive devices equally well as with more complicated devices, whenever the actual immunoassay or DNA hybridization is done with the porous film on the surface of EChip (CIPF-EChip device). Thus, a considerable improvement to earlier CIPF devices is obtained, the measuring instrument and the measuring cartridge are cheap enough for the point-of-need analyses and can be manufactured to be fully disposable. Thus, no carry-over between analyses can occur and the manufacturing of CIPF-Echip cartridges will become much easier when no separate working electrodes and counter electrodes are introduced in the cartridge. Although the best performance is obtained with porous film over the electrodes, the present invention is not limited to the use of the film. Omitting the film may only increase the time needed for the bioreactions.

The normal working electrode materials of HECL, silicon and aluminum, form anodic oxide films as anodes and therefore cannot be used as anodes in HECL cells. There are two reasons for this. First, the anodic oxidation will prevent the current flow in the cell very fast after few excitation pulses. Second, anodic oxidation produces strong electroluminescence also known as galvanoluminescence in the older literature (S. Ikonopisov, Electrochimica Acta, 20 (1975) 783-793.)

We incidentally found out that the above problem can be avoided when the anode fabricated from aluminum or silicon is painted with carbon paste. Thus, an easy way of fabricating low-cost EChips is vacuum evaporating aluminum or silicon electrodes on an insulating support such as glass or plastics strips and then the anode part of the electrode system is printed or painted to be finally covered with a carbon paste ink.

Second, a less preferable method was to make the upper layer from silver paint. Silver is anodically dissolvable, but normally it can withstand anodic current through the required measuring time, if the silver film is sufficiently thick.

A third experimentally found feasible way of solving the problem was to coat both the anode and cathode portions of the EChip with an organic polymer which produces a flawless film. This, is highly important invention, because this type of electrodes produce ECL from lanthanide chelates and possibly also from other luminophores. The exact luminescence mechanism can, however, only be speculated, because at the anode, the hot electron tunneling should not be possible at all.

An embodiment of the present invention is that, first, the electrode is fabricated with conventional methods used in HECL either from silicon or aluminum (either from bulk or film) and a thick (>100 nm) insulating film is fabricated by printing or painting with an insulating ink over the intended anode areas. This is followed by printing the anodes over the insulating film with a conducting ink or paint such as, carbon paste, silver or other metal paint or conductive polymer.

The preset invention discloses different variants of CIPF-EChip. Chips can be used with or without CIPF as simple versions of strips or sticks. However, these examples wish to illustrate the basic principles of the present invention only. The Examples demonstrate that the simple design can be included in more complex devices as an operational luminescent unit. Such cartridges can be produced in different ways and can include tubings, channels and cavities. Many cartridge constructions which are published can readily accommodate the HECL electrodes of the present invention.

The present invention forms a significant improvement over the prior art as to devices and methods intended especially onto the point-of-need applications by making possible manufacturing of convenient, cheap, quantitative rapid test strips and test cartridges. The EChips described in the present invention were primarily designed to be used with Labmaster PiiaII luminescence reader (www.Labmaster.fi) with removable counter electrode (normal PiiaII strips utilize the counter electrode situated inside of the PiiaII instrument). The miniature variants of the present EChips can easily be combined to cartridges made of plastic, PDMS etc. which allow the use the membranes of the CIPF devices whenever necessary but also other types cartridges are easily conceivable based on the construction and materials advised in the present invention.

An integral part of this invention is that bipolar pulsing can be used to excite certain combinations of constructions and materials of the present EChips. The advantage is that the combined (anode and cathode) electrode areas serve as the work electrode at some stage of bipolar pulsing and, thus, a bioaffinity assay can carried out on the surface of all the parts of the electrode network on the actual cell area of the EChips. While the bipolar pulsing is here exemplified in rather simple versions including only a few combinations of constructions of electrodes and materials, it should be understood that the same principles can be logically enlargened to other materials and constructions.

Next, the invention will be illustrated further by diagrams and non-limiting examples and figures linked to them.

EXAMPLE 1

Figure 1:
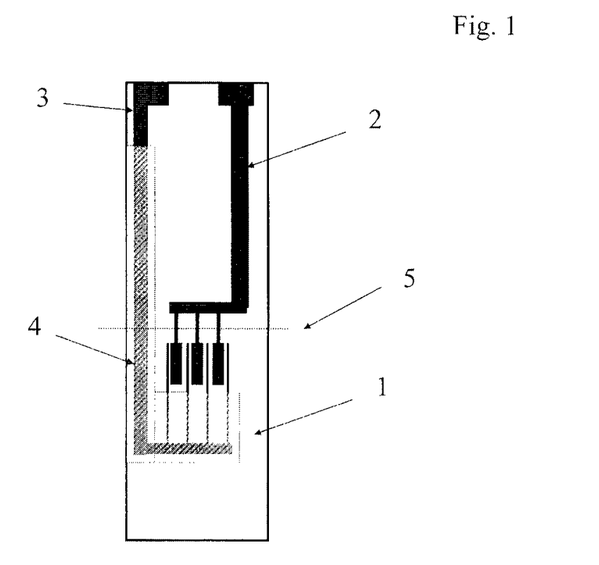
FIG. 1. A schematic diagram of an EChip composed of an insulating support (1) onto which a thin insulating film-coated work electrode (2) is fabricated e.g. by vacuum evaporation or sputtering and/atomic layer deposition and a counter electrode (3) also by vacuum evaporation or sputtering, and an insulating polymer film (thickness of the order of 100 nm or more) or an adhesive tape which prevents other parts of the counter electrode, except the area intended to be a part of an electrolytic cell, getting into contact when EChip is immersed in the electrolyte solution to the level (5) required for the HECL measurement.

Fabrication of Different Types of EChips and Measuring the Calibration Plots of Tb(III) Labels EChips of type described in FIG. 1 were fabricated by cutting first a polystyrene strip of size 12.0×75.0 mm. Then a short plasma etching stage was carried out to clean the surface, and a chromium layer was vacuum evaporated on the electrode areas through a mask followed by another layer of metal but now 99.99% pure aluminum. Aluminum was let to be oxidized for 24 hours at the room temperature and then the counter electrode areas were either painted by small brush through a mask simulating thus screen-printing with a silver ink (Bison Electro G-22, Bison Ltd, Netherlands). The surface area ratio of 5:1 between the electrodes (work/counter) was observed to be very well working, and with bare eyes in the dark room to show very even light emission from the whole work electrode areas when 0.0001 M Tb(III) chelate solution was cathodically excited in 0.05 M sodium tetra borate buffer containing 0.001 M peroxodisulfate. These EChips types were used in obtaining results of FIG. 1 (a), points marked with closed circles. The problem with these types of counter electrodes is that they are slowly dissolving anodically during measurements.

Figure 3:
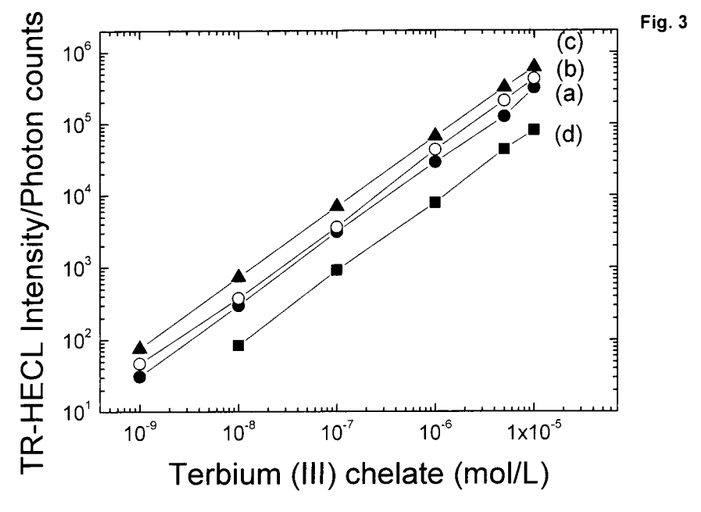

However, this problem could be solved by adding a carbon paste ink (Creative Materials 110-04 Carbon Ink, Tyngsboro, Mass., USA) layer on top of the silver ink layer. Results of FIG. 3 (b), points marked with open circles, and FIGS. 4 (a) and (b) were obtained by these types of EChips. Third solution in prevention of deterioration of aluminum anodes during measurements were observed to be very short dipping (except the uppermost area of the EChip) in toluene containing 0.1 mg/mL polystyrene and letting the toluene to be evaporated away. If the dipping were carried out too sluggishly a part of the electrode areas tended to be peeling off, thus later glass support was used instead of polystyrene. The results of these types of EChips are presented in FIG. 3 (d), points marked with squares.

The large EChips of type described in FIG. 2 were fabricated as follows. The oxidation of Si wafers. The wafers (Si wafers: resistivity 0.01-0.023 Ωcm, p++ boron-doped, orientation <100>, thickness 525+/−25 μm, producer Okmetic Oyj) were washed the RCA washing generally used in industry and were placed into an oven at 700° C., where the atmosphere contained 95% nitrogen, and 5% oxygen. The temperature was increased to 850° C. and oxygen partial pressure was increased: 90% nitrogen, 10% oxygen and incubated for 35 minutes. The wafers were rinsed with pure nitrogen flow for 30 min. The temperature was decreased back to 700° C. in pure nitrogen and the wafers were removed from the oven. The wafer to be sliced was attached to slicing base and was sliced by computer controlled diamond blade saw into the size of Si strip needed.

Figure 5:
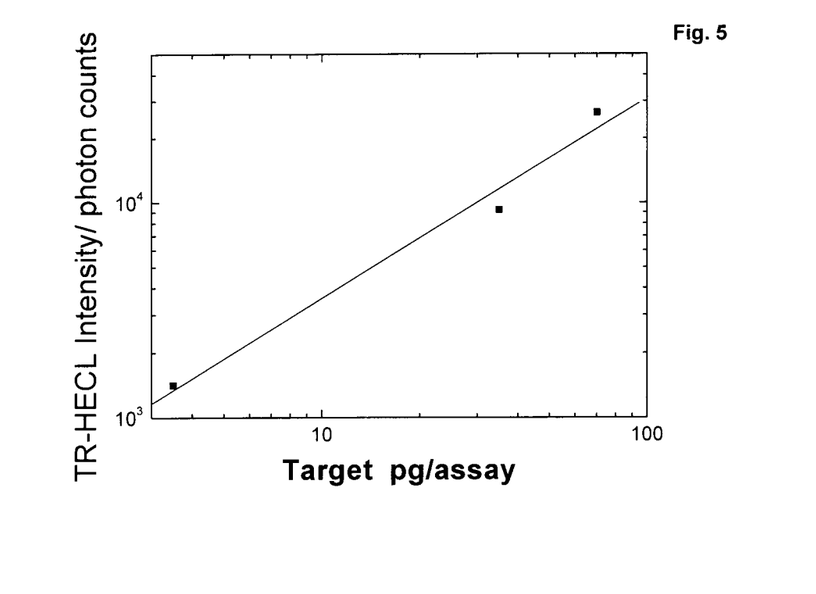
Figure 6:
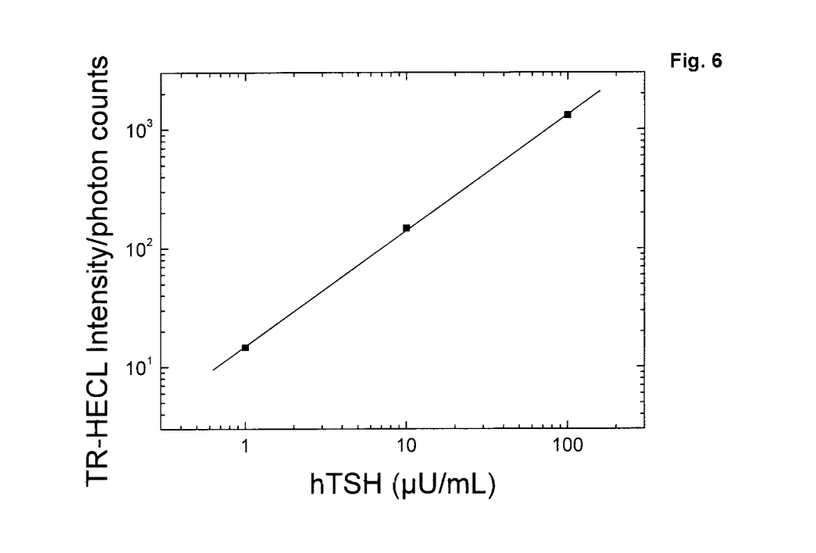
FIG. 6. Calibration curve of heterogeneous hTSH immunoassay with standard samples. Electrodes on the EChip are made of aluminum and coated with a thin polystyrene film. Bipolar excitation pulses were used (see Example 4).

After this, a plastic adhesive tape was added to the top of the EChip leaving three working electrode areas exposed (FIG. 2) Then counter electrode areas were painted through the mask with Bison silver ink (Bison electro G-22, Bison Inc, Netherlands). Silver ink was further coated with carbon paste through a mask (Creative Materials 110-04 Carbon Ink, Tyngsboro, Mass., USA) when the first silver layer was totally dry. The results obtained with these electrodes are presented in FIG. 3 (c), points marked with triangles. The results of FIG. 5 were also obtained with these types of EChips.

EXAMPLE 2

Heterogeneous TSH Immunoassay with Standard Samples and Whole Blood Samples

The EChips used for heterogeneous TSH immunoassay are similar to those of described in FIG. 1.

Working electrodes were coated using adhesive tape to form a well around the electrode area. The coating solution (300 μL) composed of 0.1 M MES, 0.03 M $H_3BO_3$, 0.5 mM K-citrate, 0.025% glutaraldehyde, 0.05% bovine gamma-globulin and 10 μg/mL of antibody (MIT0406 MOAB anti hTSH Medix Biotech Inc. USA). After incubation for two hours at room temperature the coating solution was aspirated and the wells were washed two times with washing solution (50 mM Tris-HCL, pH 7.8, containing 0.9% of NaCl, 0.09% $NaN_3$ and 0.05% Tween 20. The wells were then saturated by adding 300 μL of saturation solution (50 mM Trizma base, 0.1% BSA, 0.1% $NaN_3$, 0.1% Tween 20, pH 7.5 adjusted with $H_2SO_4$). After saturation the adhesive tape was removed from around the electrode area and the trips were allowed to dry at 30° C. for 2.5 hours.

Labeled antibody (monoclonal anti-hTSH, clone 5404, 5.5 mg/mL, Medix Biochemica Oy Ab) was prepared by allowing an isothiocyanate derivative of Terbium (III) chelate (Tb-2,6-bis[N,N-bis(carboksymethyl)aminomethyl]-4-bent-soylphenol chelate) to react in 80 times molar excess at pH 9.5 for over night at room temperature. A column 1 cm in diameter filled to 5.5 cm with Sephadex G-50 and for a further 52 cm with Sepharose 6B was used to separate the conjugated protein fraction from excess reagent.

The immunoassay was based on the use of porous film. Porous film (thickness 6-11 um, $1 \times 10^5$-$6 \times 10^8$ holes/$cm^2$, Whatman) was attached to the tape frame having opening to cover the electrode area of the test strip. The labeled antibody (0.5 μL, 80 μg/mL) in 50 mM Tris-HCl buffer, pH 7.7, containing 0.05% $NaN_3$, 0.9% NaCl, 0.5% BSA, 0.05% bovine gammaglobulin and 0.01% Tween 20 was pipetted onto the membrane and allowed to dry at room temperature over night.

The standard samples (TSH concentrations 0.1, 1.0, 10.0 and 100.0 mIU/L) were prepared in test tubes by diluting TSH standard solution (Wallac, DELFIA hTSH kit, 324 mIU/mL TSH) with dilution solution (50 mM Trizma base, 0.05% $NaN_3$, 0.9% NaCl, 0.5% BSA, 1 mM $CaCl_2*H_2O$, pH 7.7 adjusted with HCl).

For the immunoassay the membrane with the frame was attached to the strip by the extension part (having also glue on it) of the frame. A 3.5 µL of sample (standard samples or heparin whole blood samples) was pipetted onto the porous film of the test strip. Sample dissolves the labeled antibody and fills fast the whole electrode area forming very thin liquid layer between the membrane and the electrode area. After 5 minutes the immunoreaction was sufficiently proceeded and the membrane frame was removed by hand. The test strip was moved into the washing/measuring cell of the electrochemiluminometer. The cell was filled 4 times and aspirated 3 times with combined washing/measuring solution (50 mM $Na_2B_4O_7$, 0.1% $NaN_3$, 0.003% Tween 20, pH 7.9 with $H_2SO_4$). After the last fill, the ECL (pulse frequency 10 Hz, pulse charge=20 µC, pulse time 250 µs, 60 pulses, U=25 V) was measured with luminescence instrument described in U.S. Pat. No. 6,251,690. After the measurement the cell was aspirated and the Si strip was removed. Typical dose responsive curves with standard samples and heparin whole blood samples are presented in FIG. 4 (*a*), points marked with circles and 4 (*b*) points marked with squares, respectively

EXAMPLE 3

Probe Assay of Viral RNA

A 120-nt PCR fragment was amplified using viral RNA as target (Lönnrot et al., J. Med. Vir. 56 (1999) 378-84.)

CNS pathogens=pathogens in Central Nervous System). This region is diagnostic target in centralized diagnostic laboratories for routine analysis of entero- and rhinoviruses, which are important respiratory and CNS pathogens.

Figure 2:
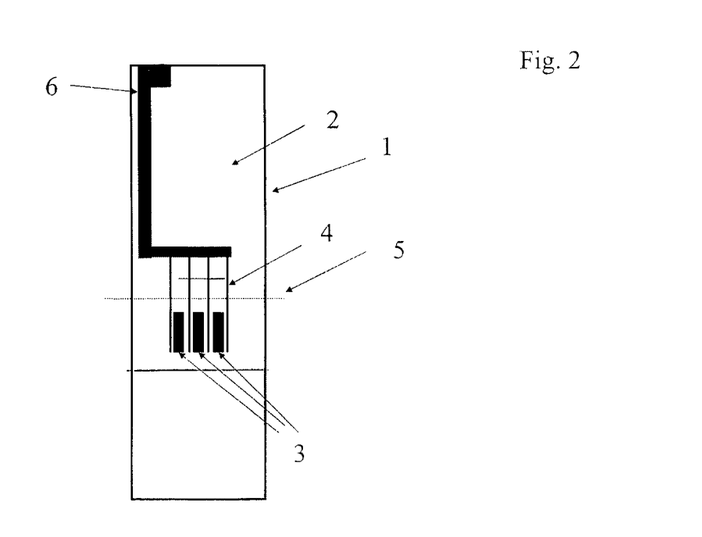
FIG. 2. A schematic diagram of a large EChip composed of a silicon or aluminum strip (1) which is first coated with a 4-nm oxide film all over, and then coated with a thick printed polymer film (thickness of the order of 100 nm or more) or adhesive tape (2) all other areas except work electrode areas (3) thus leaving three 4-nm oxide-coated work electrode areas exposed top the final electrolytic cell (marked with grey color). On the thick insulator film (2) the counter electrodes (4) are either printed with conducting ink such as carbon paste or silver ink or conducting polymer, or fabricated by vacuum evaporation or sputtering from a metal. The final electrolyte solution level is marked with (5). Electronic contact to the work electrode is taken behind the specimen and to the counter electrode from a contact pad (6).

Cathcing probe (C-probe, TTA-GCC-GCA-TTC-AGG-GGG-CGA-AAA-AA-C6-NH2 (SEQ ID NO:1), MedProbe As) complementary to the template strand of the 5'-end of picorna-RNA was immobilized to oxide-coated silicon electrodes (IEChip, FIG. 2, Example 3). The C-probe was designed to have polyA-tail followed by specific primer to which denatured PCR product was allowed to anneal. The catching probe was bound to silanized (APTES) silicon surface by the six carbon aliphatic carbon and end amino group via DSS-reagent (disuccinimidyl suberate) according to manufactures instructions.

The detection probe (NH2)4-GA-AAC-ACG-GAC-ACC-CAA-AGT-A) (SEQ ID NO:2)) was labelled with the isothiocyanate derivative of Terbium-chelate (Tb-2,6-bis[N,N-bis (carboxymethy)aminomethyl]-4-benzoylphenol chelate) by incubating the probe with 80 times higher molar excess of the chelate in 0.5 molar sodium carbonate buffer (pH 9.5). After over night incubation the labeled probe was purified by Sephadex G50 column (NAP-5 column, GE Healthcare)

Hybridization assay of human entero- and rhinoviruses was done as follows. After RT-PCR amplification, the DNA sample (PCR amplified sample diluted 1:50, 1:100 and 1:1000, 20 µL) was denaturated by adding 1804 of 50 mmol/L NaOH (5 min at 37° C.) and the neutralized by adding 200 µL of neutralization buffer (6×SSC, 0.3% Tween 20, 20 mmol/L citric acid). Thereafter 10 µL of this neutralized sample and 10 µL of Tb-labeled probe (0.6 ng/µL, 50 mmol/L Tris-HCl buffer, pH 7.8, 600 mmol/L NaCl, 1% Triton X 100 and 1% Blocking reagent (Roche) were taken into a new tube and after mixing finally 3.5 µL of this solution was taken onto the test strip. The test strip contained the membrane with the frame as in Example 2. After 5 minutes at ambient temperature the reaction stops and after removing the membrane from above the silicon chip, the test strip was washed 3 times and the TR-CECL measured by the PiiA reader. The sample dilution curve is presented in FIG. 5. The concentration of the PCR amplified sample was estimated to be 40 ng/µL.

EXAMPLE 4

Heterogeneous TSH Immunoassay with Standard Samples with Bare Aluminum Oxide-Coated Electrodes and the Similar Electrodes Additionally Coated with a Thin Polystyrene Film First, EChips containing electrodes made of evaporated aluminum on a glass slide (12.0×75.0 mm) were fabricated analogously to those in the Example 1 in the case of polystyrene strips. Then, the electrodes were shortly sonicated in ultrasonic bath in benzene solution containing 0.1 mg/mL and lifted slowly from the polystyrene solution. During evaporation of benzene a thin film of polystyrene was formed on top of the electrodes. Polystyrene coating was omitted from a batch of EChips to be used in bipolar measurements.

First, the EChips fabricated without the final polystyrene film were used in a heterogeneous immunoassay of hTSH analogously to the Example 2. The measurement was carried out so that the electrode polarity was changed during the measurement with DPDT switch (double-pole-double-throw, on-on-on, cross linked output positions, input in the middle position) after each 10 excitation pulses, 60 excitation cycles were used altogether. TR-HECL intensity obtained was quite low, but anyway the final signal weakly corresponded to the concentration of hTSH (FIG. 4 (*a*), results marked with squares.

Figure 4:
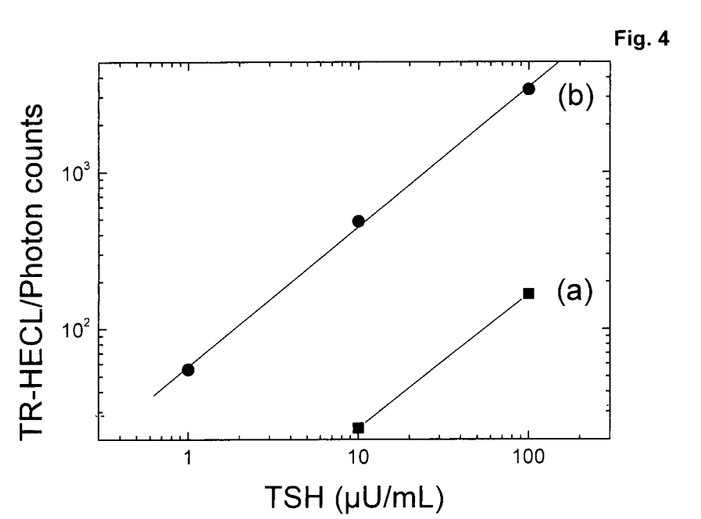
FIG. 4. Calibration curve of heterogeneous hTSH immunoassay with standard samples (a) (squares) and whole blood samples (b) (circles). hTSH-standards were prepared in heparinized whole blood sample. The measurements were done using a membrane of a standard Labmaster CIPF device (Labmaster Ltd., Turku, Finland) containing all the required immunoassay reagents in dry state on top of the work electrode and counter electrode areas of the type of EChip described in FIG. 1 (see Example 2).

When EChips coated with a thin polystyrene film were used, considerably better results were obtained (FIG. 4 (*b*), circles), both the background signal was lower and the emission of the labels was higher. It is believed, that much better results can be obtained if the coating of the electrodes with an organic substance, possibly with even better suitable polymer is carried out and the film thickness is also optimized.

EXAMPLE 5

Homogeneous hTSH Immunoassay with Standard Sample Solutions in PDMS-EChip Cartridge The PDMS fluidic chip was fabricated by casting Sylgard 184 silicone elastomer, base and curing agent mixed in a 10:1 ratio, onto the master mold in a Petri dish. The wet PDMS was then out gassed in vacuum and cured at 50 C. for 2 hours. The cured PDMS was peeled off the master, cut into individual chips, and bonded to the HECL electrode chips. Bonding was improved by first exposing both the PDMS fluidic chip and the HECL electrode chip to oxygen plasma in a Technics Plasma TePla-400 reactor for 30 seconds, using 800 sccm oxygen flow and 800 W RF power. This plasma treatment also makes the PDMS surface hydrophilic, enabling filling of the sample chamber by capillary force.

In the PDMS lid there is a small input chamber in the left (See FIG. 7) wherein all the necessary reagents are dried prior to analysis. Inlet channels at one end of the entrance chamber of the chip are used to fill the incubation and measuring chamber by capillary forces and hydrostatic pressure while multiple outlet channels allow air to escape during filling of the combined incubation and measuring chamber. Small pillars support the chamber's PDMS ceiling. In the current design, the pillars are evenly distributed throughout the fluidic chamber. The height of the measuring and incubation cavity was 0, 35 mm. The PDMS lid covers only the electrode area of the HECL chip, leaving the electrical contact pads exposed. The total thickness of the PDMS lid was 5.0 mm.

Figure 7:
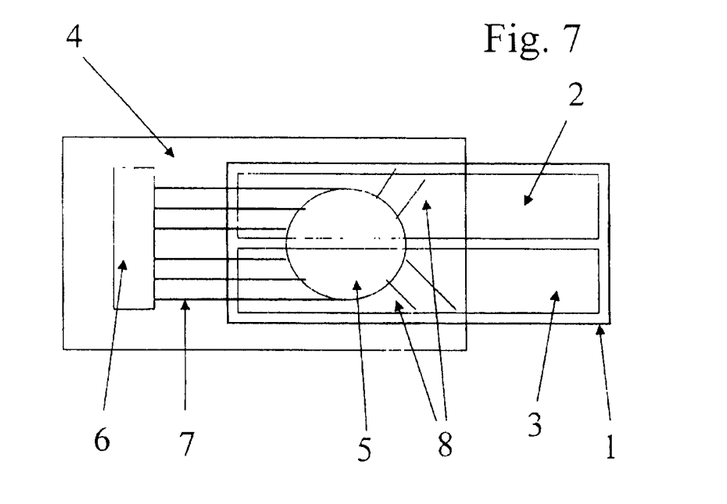
FIG. 7. A disposable EChip cartridge composed of PDMS lid and an EChip. (1) EChip support base (e.g. glass, plastic or silicon), (2) Work electrode (e.g. oxide-coated aluminum with some optional additive layer or alternatively oxide-coated silicon is exposed under this area from a field withstanding thick insulator layer, (3) Counter electrode (in case of aluminum or silicon preferably coated with carbon paste), (4) PDMS lid, (5) Incubation/measuring chamber in the PDMS lid, (6) Reagent and Sample addition chamber (open upwards), (7) Micro channels feeding the Incubation/measuring chamber, (8) Air outlet micro channels.

First, a glass chips of size 19.0 mm×10.0 mm, were shortly plasma etched and then approximately a 0.5-mm layer of aluminum was vacuum evaporated on the chips through a mask, thus, making both of the electrode areas (2 and 3 in FIG. 7). The one intended to be cathode (2) was oxidized in oxygen atmosphere at room temperature, but the one intended to be an anode (3) was painted with a carbon paste through a mask (Creative Materials 110-04 Carbon Ink, Tyngsboro, Mass., USA.).

Human TSH assay was used as a model bioaffinity assay here. The monoclonal anti-TSH primary antibodies (catching antibodies) specific to the α-chain of hTSH (MOAB, lot: M-21310, catalogue number MIT0406, conc. 6.87 mg/ml) were purchased from Medix Inc, USA and a secondary monoclonal anti-TSH specific to the β-chain of hTSH (clone 5404, lot SPC099, conc. 5.5 mg/ml) from Medix Biochemica Oy Ab, Finland. The hTSH calibration standards were obtained from Orion Diagnostica, Finland. 4-morpholineethanesulfonic acid (MES) and boric acid were obtained from BDH Chemicals Ltd, Poole, England and Merck, respectively. Potassium citrate, glutaraldehyde (GA), bovine-γ-globulin, Tris and bovine serum albumin (BSA) were products of Sigma. $Na_2B_4O_7 \cdot 10H_2O$, and $NaN_3$ were pro analysi products of Merck.

After the carbon paste had been cured, the intended immunoassays areas were coated with primary antibody as follows below.

The final electrode area of the chips were coated with the primary antibody by physical adsorption by incubating the electrode in a buffer containing 0.1 M MES, 0.3 M boric acid, 0.025% bovine gamma globulin (pH 6.5) and the primary antibody (MOAB, lot: M-21310, Medix Inc, USA) 30 μg/ml for 3.0 h in a micro well formed by an adhesive tape with a round whole in its center, a bit larger than the final electrolytic cell area. After coating, the surface was washed with buffer solution and equilibrated for one hour in 0.05 M Tris-$H_2SO_4$ buffer, pH 7.75, containing 0.1% bovine serum albumin, 0.1% Tween 20 and 0.1% $NaN_3$.

Next, the PDMS lid (size 25 mm×14 mm, 5 mm thick; 4 in FIG. 7) was clamped in the right position with the EChip and 100 ng/of the secondary antibody were dried in the first sample cavity of the PDMS-EChip (6 in FIG. 7).

Immunoassays were carried out in 0.2 M borate buffer adjusted to pH 7.8 with sulphuric acid. First, 25 μl of standard and 175 μl assay buffer (0.2 mol/l borate-$H_2SO_4$, pH 7.8, 0.1% $NaN_3$, 0.5% bovine serum albumin, 0.05% bovine gamma globulin and 0.01% Tween 20, 0.01 M $NaN_3$) were mixed and added to the sample cavity (6 in FIG. 7).

Figure 8:
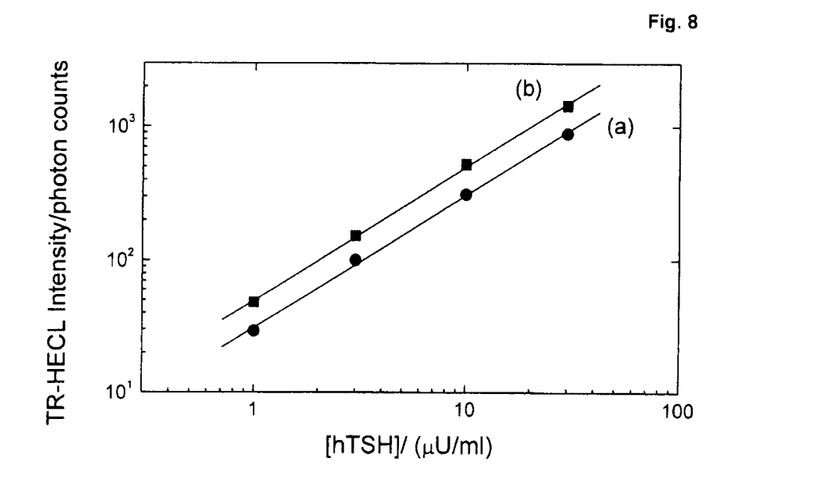
FIG. 8. Homogeneous hTSH immunoassay with standard sample solutions (see Example 5). (a) Oxide-coated aluminum work electrode, circles (b) Oxide-coated silicon work electrode, squares.

Then the added solution first dissolved the dried label from the first chamber, and the hydrostatic pressure and capillary forces filled the final electrolytic cell area (5 in FIG. 7) through input micro channels (7 in FIG. 7) while air was removing through small outlet channels (8 in FIG. 7). After 15 minutes of incubation the HECL intensity was measured; the results are presented in FIG. 8 (*a*), points marked with circles. Measuring instrument was composed of Stanford Research Instruments SR 400 gated photon counter, Nucleus MCS multiscaler card and home made coulostatic pulse generator and home made cell compartment (black plastic) and Perkin-Elmer photon counting CPM module. Pulse amplitude was −25 V, pulse charge 15 μC/pulse, pulse frequency 20 Hz, the TR-HECL intensity was integrated over 200 excitation cycles, delay time 0.05 ms and gate time 6.0 ms.

Analogous measurements were carried also by using EChips which were fabricated from silicon chips (10×19 mm) wherein the whole surface was first thermally oxidized with our normal procedures described above to produce a 4-nm oxide film thickness. Then, an adhesive tape was added to the chips leaving the electrode areas exposed. The intended anode was then painted through a mask with the same carbon paste used in the examples above. Otherwise, the immunoassays were carried out similarly to those described above in this example and the results are presented in FIG. 8 (*b*), points marked with squares.

The invention claimed is:

1. An electrochemiluminescent analytical device to determine an amount of an analyte, said device comprising electrode chip and a hot electrochemiluminescense instrument (HECL), wherein:
   a working electrode serving as a cathode and a counter electrode serving as an anode are integrated on the chip, and the anode and cathode are connected to the HECL via pads providing an electronic contact;
   the anode and cathode are constructed on same substrate, said substrate providing a basis of an electrode chip and said substrate being made of an insulating material or partially of conducting and partially of insulating material;
   the anode and the cathode being made from aluminum or silicon, and the anode successively comprising an insulating film of a thickness of at least 100 nm and coated with an oxide layer of 0.5-50 nm and a carbon paste or silver ink layer, and the cathode being successively coated with an oxide layer 0.5-20 nm and an insulating organic film of 0.5 to 20 nm;
   wherein during or after applying cathodic or bipolar pulses to the device from the HECL instrument a luminescence signal can be read from the device during, said signal being proportional to the amount of the analyte.

2. The device according to claim 1, wherein:
   the working electrode and the counter electrode have contact strips to opposite end of the electrode chip through which the electrodes can be connected to excitation electronics of the HECL instrument,
   and wherein after or during applying excitation pulses a sample to be analyzed will yield luminescence signal which is proportional to the amount of the analyte.

3. The device according to claim 1, wherein both of the electrodes are made of silicon or aluminum and their surfaces contain an ultra-thin oxide layer of 0.5-20 nm which are successively coated with an additional ultra-thin insulating organic substance film of 0.5-20 nm.

4. The device according to claim 1, wherein
   The electrode chip containing the cathode and the anode is integrated in a cartridge, said cartridge having an entrance inlet and a multitude of cavities, where the cavities of the cartridge are capable to be filled either by capillary forces, pressure, or suction,
   and wherein when a sample or a diluted sample is filling the cavities it dissolves all the necessary reagents from the entrance inlet, and the sample is capable to give luminescence signal which is proportional to the amount of the analyte.

5. The device according to claim 4, wherein the cavities are capable of being washed with a solution prior to excitation.

6. A method for a bioaffinity analysis comprising the steps of:
   a) providing a device of claim 1;
   b) inserting a test strip containing immunoassay reagents in a dry state on top of the work electrode and counter electrode;
   c) adding a sample on the strip;
   d) allowing an immunoreaction to proceed;
   e) allowing the electrode to excite the label;
   e) removing and washing the strip;
   f) measuring light emitted from the label, and
   g) determining amount of analyte in the sample by referring to prior created standard curves.

7. The method of claim 6, wherein the method comprises applying cathodic or bipolar excitation pulses or trains of said pulses to the electrodes.

8. The method of claim 6, wherein the bioaffinity analysis is a nucleic acid probing assay or immunoassay.

9. The device of claim 1, wherein a porous film of a thickness less than 100 μm is brought onto the electrodes, said film being capable of receiving a sample to be analyzed and reagents to accomplish a bioaffinity reaction, and the sample being capable to give a luminescence signal proportional to the amount of analyte during or after cathodic or bipolar pulses.

* * * * *